(12) United States Patent
Cecere et al.

(10) Patent No.: US 8,758,257 B2
(45) Date of Patent: Jun. 24, 2014

(54) INSTRUMENT INCLUDING A MOVEMENT SENSOR FOR POSITIONING AN EFFECTIVE PORTION AND METHOD OF USING SAME

(76) Inventors: Renzo Cecere, Ville Mont Royal (CA); Toufic Azar, Westmount (CA)

( * ) Notice: Subject to any disclaimer, the term of this patent is extended or adjusted under 35 U.S.C. 154(b) by 643 days.

(21) Appl. No.: 12/926,915

(22) Filed: Dec. 17, 2010

(65) Prior Publication Data

US 2011/0160596 A1 Jun. 30, 2011

Related U.S. Application Data

(60) Provisional application No. 61/282,177, filed on Dec. 24, 2009.

(51) Int. Cl.
*A61B 5/02* (2006.01)

(52) U.S. Cl.
USPC .......................... 600/481; 600/508; 600/595

(58) Field of Classification Search
CPC ............... A61B 5/11; A61B 2562/028; A61B 5/02028; A61B 5/021; A61B 5/0456; A61B 5/0452; A61B 5/1102
USPC ........................................................ 600/481
See application file for complete search history.

(56) References Cited

U.S. PATENT DOCUMENTS

| | | | |
|---|---|---|---|
| 6,913,608 | B2 | 7/2005 | Liddicoat et al. |
| 6,986,775 | B2 | 1/2006 | Morales et al. |
| 7,037,334 | B1 | 5/2006 | Hlavka et al. |
| 7,090,637 | B2 | 8/2006 | Danitz et al. |
| 7,166,127 | B2 | 1/2007 | Spence et al. |
| 7,233,821 | B2 * | 6/2007 | Hettrick et al. ............... 600/510 |
| 7,371,210 | B2 | 5/2008 | Brock et al. |
| 7,431,726 | B2 | 10/2008 | Spence et al. |
| 2003/0139668 | A1 * | 7/2003 | Ben-Haim et al. ............ 600/424 |
| 2005/0119523 | A1 | 6/2005 | Starksen et al. |
| 2006/0111615 | A1 | 5/2006 | Danitz et al. |
| 2007/0276437 | A1 | 11/2007 | Call et al. |
| 2008/0051838 | A1 * | 2/2008 | Shuros et al. ..................... 607/2 |
| 2008/0058591 | A1 | 3/2008 | Saadat et al. |
| 2008/0097476 | A1 | 4/2008 | Peh et al. |
| 2008/0214889 | A1 | 9/2008 | Saadat et al. |
| 2008/0228198 | A1 | 9/2008 | Traynor et al. |
| 2008/0228267 | A1 | 9/2008 | Spence et al. |
| 2008/0234728 | A1 | 9/2008 | Starksen et al. |

(Continued)

OTHER PUBLICATIONS

Toufic Azar et al. "A Concept for a Novel Procedure for Mitral Valve Repair by Percutaneous Annuloplasty", Proceedings of BioMed2008 3rd Frontiers in Biomedical Devices Conference Jun. 2008, Irvine, California, USA, pp. 33-34.

(Continued)

*Primary Examiner* — Michael Kahelin
*Assistant Examiner* — Karen Toth

(57) ABSTRACT

An instrument positionable with respect to a body valve in the body of a living subject for performing a predetermined procedure on the living subject at a predetermined location relative to the body valve. The instrument includes: a movement sensor for sensing movements of the body valve; an effective portion for performing the predetermined procedure when the effective portion is at the predetermined location; and an effective portion positioner for positioning the effective portion in the living subject. The effective portion is positionable using the effective portion positioner in response to the movements sensed by the movement sensor for positioning the effective portion at the predetermined location in order to perform the predetermined procedure.

15 Claims, 7 Drawing Sheets

(56) References Cited

U.S. PATENT DOCUMENTS

Figure 1:
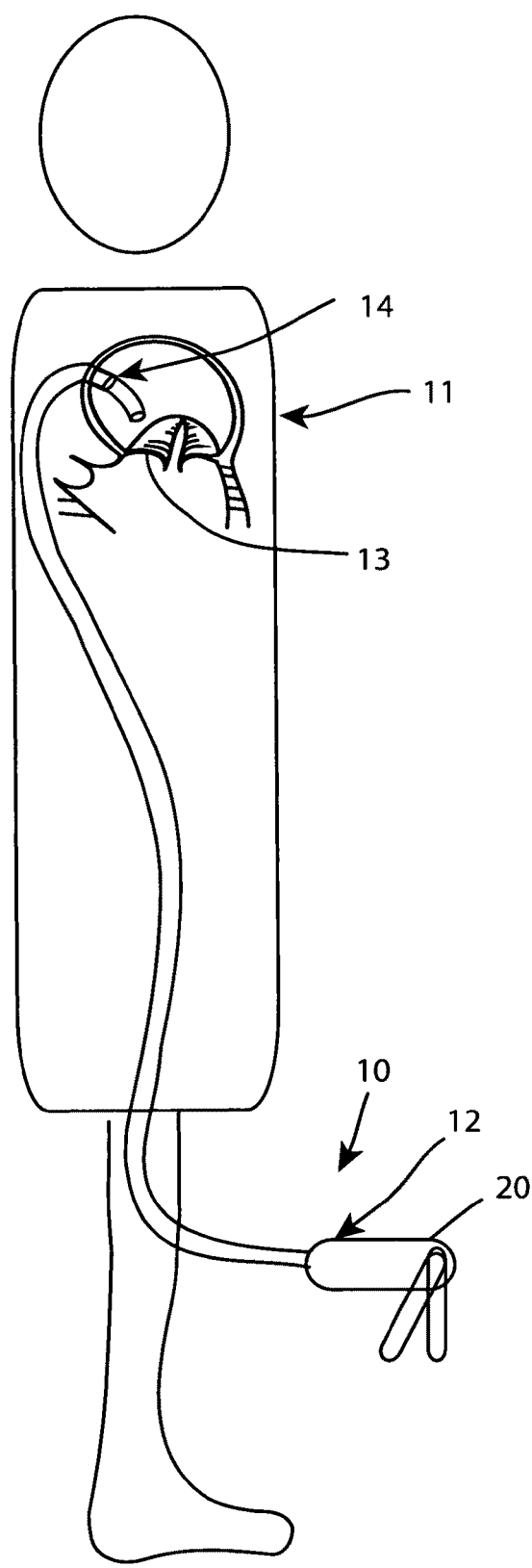

| | | |
|---|---|---|
| 2008/0234815 A1 | 9/2008 | Starksen |
| 2008/0243150 A1 | 10/2008 | Starksen et al. |
| 2008/0255505 A1 | 10/2008 | Carlson et al. |
| 2008/0275503 A1 | 11/2008 | Spence et al. |
| 2008/0285909 A1 | 11/2008 | Younge et al. |
| 2008/0294177 A1 | 11/2008 | To et al. |
| 2009/0076476 A1 | 3/2009 | Barbagli et al. |
| 2009/0076498 A1 | 3/2009 | Saadat et al. |
| 2009/0076547 A1 | 3/2009 | Sugimoto et al. |
| 2009/0270741 A1* | 10/2009 | Vanney et al. ............... 600/486 |
| 2010/0114220 A1* | 5/2010 | Paradis ............................ 607/6 |
| 2010/0280366 A1* | 11/2010 | Arne et al. ..................... 600/425 |

OTHER PUBLICATIONS

Toufic Azar et al. "A Concept for a Novel Procedure for Mitral Valve Repair by Percutaneous Annuloplasty", Slides presented at BioMed2008 3rd Frontiers in Biomedical Devices Conference, Jun. 2008, Irvine, California, USA.

Laurens F. Tops et al., "Percutaneous Valve Procedures: An Update", Aug. 2008, Curr Probl Cardiol, pp. 417-457.

* cited by examiner

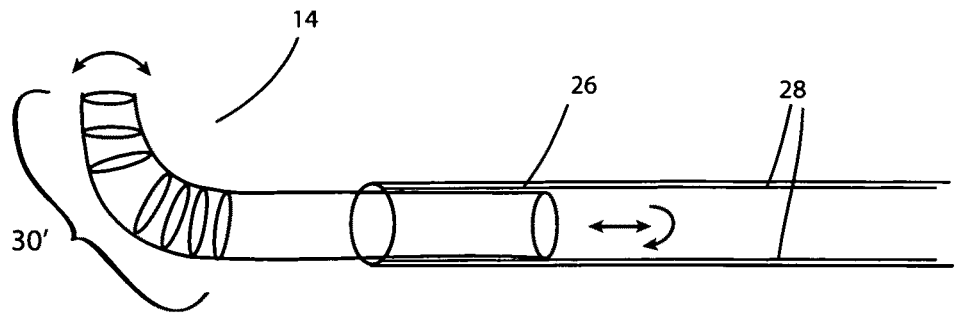
Fig. 3
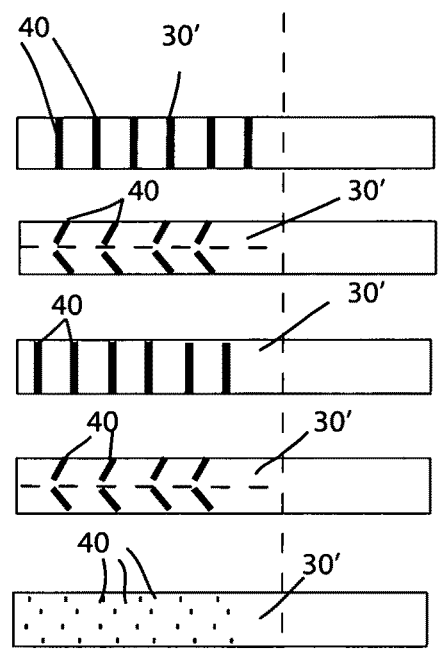
Fig. 4A
Fig. 4B
Fig. 4C
Fig. 4D
Fig. 4E
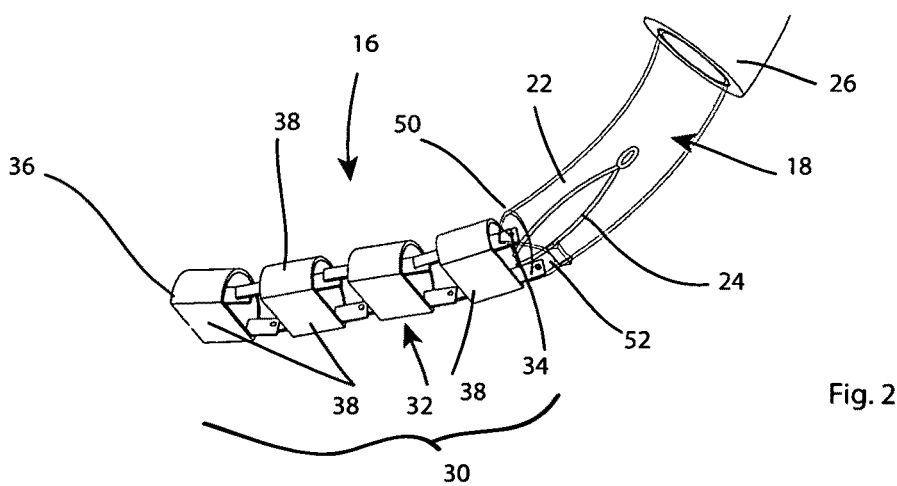
Fig. 2 ously. In particular, since the annulus function is to support the leaflets, any variation in its geometry, will directly affect the closure of the leaflets and the valve area.
INSTRUMENT INCLUDING A MOVEMENT SENSOR FOR POSITIONING AN EFFECTIVE PORTION AND METHOD OF USING SAME This application claims priority from U.S. Provisional Patent Application Ser. No. 61/282,177 filed Dec. 24, 2009, the contents of which is hereby incorporated by reference in its entirety

FIELD OF THE INVENTION

The present invention relates to general field of instrument positioning. More specifically, the present invention is concerned with an instrument including a movement sensor and a method of using the same for positioning an effective portion of the instrument.

BACKGROUND

Mitral valve regurgitation (MR) is a functional heart disease under which the valve does not close completely and causes blood to leak back into the left atrium. This condition increases the workload on the heart and, if left untreated, can lead to irreversible heart damage, cardiac arrhythmia and congestive heart failure. Currently, mitral valve repair, as the intervention is called, requires open heart surgery with cardiopulmonary bypass. Under such conditions, the patient is subjected to intra- and post-operative trauma that can result in mortality increase and that can prevent high-risk individuals from undergoing the intervention. Hence the need to develop alternative procedures such as minimally invasive percutaneous interventions, which would greatly reduce the trauma and risks associated with conventional surgery, resulting in an increase of the number of potential candidates for repair, while significantly cutting patient's recovery times from weeks to days.

More specifically, a heart condition is often the result of a weakened heart caused by many factors such as age and lifestyle, among others. This weakening is manifested in an enlargement of the organ, which can affect the valve closing. Moreover, when a valve is affected by a disease, its malfunctioning deteriorates the myocardium's normal performance.

When the mitral valve leaks, blood flows backwards into the lungs. Under these conditions, the ventricle must pump more blood with each contraction to produce the same forward output of blood throughout the body. The heart, through remodeling, can compensate for this volume overload for many months or years. However, an enlargement of the left ventricle will eventually lead to annulus dilation and/or restricted leaflet motion, which will aggravate MR; an unstable system develops, where the heart is trapped in vicious cycle leading, ultimately, to its failure. For effective treatment, it is necessary to stop the cycle and, if possible, reverse the induced anatomical changes. The severity of MR is required to guide the patient's subsequent management and is assessed using different quantitative parameters.

Chronic MR is usually classified in three categories mild (1+), moderate (2+, 3+) and severe (4+). Generally the bigger the regurgitant volume, the more severe the patient condition. Mitral valve repair is usually required for symptomatic patients with a 3+ and 4+ angiographic grade. To function properly, the mitral valve requires the coordinated function of its different elements, as well as both left cardiac chambers: if one of these structures malfunctions, MR eventually occurs. In particular, since the annulus function is to support the leaflets, any variation in its geometry, will directly affect the closure of the leaflets and the valve area.

Over the years, annuloplasty has been the foundation of surgical mitral valve repair. There are two general methods of open-heart annuloplasty: (i) suture-based (rarely used) and (ii) ring-based. The former consists of a semi-circular reduction of the annulus in the posterior portion. In theory, the technique offers advantages over ring annuloplasty, as it conserves the dynamics of the valve and preserves its saddle shape; however, this remains to be clinically proven. Short-term and midterm results have shown effectiveness. On the long term, a trend toward recurrence of annular dilation was observed. An example of a current ring-based open-heart intervention involves suturing the annulus to a prosthetic ring that reduces the valve area to normal or undersized systolic dimensions. Its advantage lies in its reproducibility, its ability to conserving dimensions over time, its low sensitivity to different dilated annulus geometries and an even stress distribution over the suture attachments, which are carefully inserted in the fibrous annulus. In functional MR of type-1/type-3b, the ring-based technique has established itself as the preferred technique with very good results. On the other hand, suture-based techniques that remodel only the posterior annulus have shown poor reproducibility and poor long-term results with a recurrence of MR.

The interest of the industry in developing percutaneous mitral valve repair is high, as reflected by the large number of companies working on the problem. Two distinct categories of repair are being developed: (i) edge-to-edge repair and (ii) annuloplasty. Mainly targeting type-2 patients, the edge-to-edge repair replicates the Alfieri stitch; this consists in installing, via a catheter, a clip or suture, at the mid-portion of the valve, intended to grasp and fasten together the leaflets, at their edge midpoints, to create a double orifice. This manoeuvre increases leaflet coaptation and eliminates focal excessive leaflet motion when present. In conventional surgery, when the edge-to-edge technique is combined with annuloplasty, results are reportedly very good. However, when annuloplasty is not used, it is less effective. A percutaneous edge-to-edge repair by itself does not result in major improvements of the condition of the patient, its application being limited. On the other hand, percutaneous annuloplasty has attracted much more interest. It is useful in all cases of mitral valve repair, regardless of the etiology, and is the main correction for type-1 and type-3b patients.

Currently, many different percutaneous annuloplasties are being developed; in direct techniques, the repair affects explicitly the annulus, while in indirect techniques, a change in proximal structure leads to annulus reshaping. Five current approaches are worth mentioning: a) indirect annuloplasty via the coronary sinus (CS); b) atrial annular cinching (indirect); c) ventricular remodeling (indirect); d) transventricular suture-based method (direct); and e) energy-based annulus-shrinkage devices that use radiofrequency (RF) at sub-ablative temperatures to produce contraction of the annulus collagen (direct). Based on the literature, direct-annuloplasty techniques are more robust than indirect techniques, since they are much less sensitive to the variation in anatomy between patients and have a higher reproducibility. For example, CS-based methods require the CS to be circumferentially adjacent, on a same plane, to the annulus, which is not always the case and a risk of squeezing the circumflex artery exists. In addition, there is no background knowledge for using other indirect techniques, and longterm effects are still unknown. It is important to note a specificity of technique (c), which addresses two issues with one device, by cinching the ventricle using a transventricular cord, it indirectly squeezes the mitral annulus while countering the ventricle dilation. Such technique is regarded by many professionals as too aggressive. A trade-of between safety and performance is observed in all the techniques; none offers comparable results to rigid-ring annuloplasty, which is strong in nearly all criteria. Technique d) above achieves a partial reduction of MR without its abolition. This is intrinsically linked to the device function of reshaping only the posterior side of the annulus. The major limitation of these technique lies in their reliance on conventional manually controlled catheter, with which interventionalists can only access, from the ventricle (retrograde approach), the posterior portion of the mitral where anchors are inserted.

There therefore seems to be a need for an improved percutaneous annuloplasty. However, such annuloplasty requires precise positioning of an instrument in the heart of a patient with respect to moving tissue, which is relatively difficult to achieve. Also, while an emphasis on cardiac interventions has been made in the previous paragraphs, there are many other situations in which positioning of an instrument with respect to a moving tissue has to be performed precisely Against this background, there exists a need in the industry to provide novel instrument positionable with respect to a moving tissue. An object of the present invention is therefore to provide improved methods and devices for positioning instruments with respect to a moving tissue.

SUMMARY OF THE INVENTION

In a first broad aspect, the invention provides an instrument positionable with respect to a body valve in the body of a living subject for performing a predetermined procedure on the living subject at a predetermined location relative to the body valve. The instrument includes: a movement sensor for sensing movements of the body valve; an effective portion for performing the predetermined procedure when the effective portion is at the predetermined location; and an effective portion positioner for positioning the effective portion in the living subject. The effective portion is positionable using the effective portion positioner in response to the movements sensed by the movement sensor for positioning the effective portion at the predetermined location in order to perform the predetermined procedure.

In a second broad aspect, the invention provides an instrument positionable with respect to a moving tissue in the body of a living subject for performing a predetermined procedure on the living subject at a predetermined location relative to the moving tissue. The instrument includes: a movement sensor for sensing movements of the moving tissue; an effective portion for performing the predetermined procedure when the effective portion is at the predetermined location; and an effective portion positioner for moving the effective portion in the living subject. The effective portion is positionable using the effective portion positioner in response to the movements sensed by the movement sensor for positioning the effective portion at the predetermined location in order to perform the predetermined procedure.

In a third broad aspect, the invention provides a method for determining the position of an effective portion of an instrument relative to a moving body valve in a living subject using a movement sensor. The method includes: inserting a movement sensor for sensing movements of the body valve in the living subject; positioning the effective portion and the movement sensor in the living subject in a predetermined positional relationship relative to each other; generating with the movement sensor movement information indicative of movements in the living subject substantially adjacent to the movement sensor; receiving the movement information; and assessing the position of the effective portion relative to the moving body valve on a basis of the movement information.

In a fourth broad aspect, the invention provides a method for determining the position of an effective portion of an instrument relative to a moving body valve in a living subject using a shape sensor integrated into the end flexible portion of an instrument. The instrument conforms to the surrounding tissue. The shape taken by the instrument distal end portion permits to identify the exact shape of the tissue thus permitting to find the appropriate geometrical features.

Advantageously, the proposed method and instrument use in-situ information to position the effective portion, which provides good spatial resolution and precision in positioning the effective portion. In some embodiments of the invention, the movement sensor has temporal resolution sufficient for allowing positioning of the effective portion adjacent to relatively rapidly moving tissues.

In some embodiments of the invention, the movement sensor includes a deformable element having a configuration, a rigidity and dimensions such that the deformable element is substantially freely deformable by the moving tissue when abutting thereagainst and a deformation sensor for sensing deformations of the deformable element. In other embodiments of the invention, the movement sensor includes a substantially rigid sensor support and a movement sensing element secured to the sensor support for detecting movements substantially adjacent to the sensor support.

The effective portion is any suitable effective portion, such as, for example and non-limitingly, an effective portion including an anchor implanting mechanism for implanting anchors at the predetermined location.

Advantageously, the proposed invention allows for performing improved mitral valve annuloplasty by reducing disadvantages of prior art instruments that present poor manoeuvrability and the lack of an intelligent system that prevent the user from accurately positioning the instrument accurately onto the mitral annulus when accessed from the atrium. Indeed, the concave shape of the surface makes it hard to position, touch down and place the catheter onto the annulus while keeping a constant contact interface and position. As a consequence, in the prior art, the user of these catheters has to rely on anatomical features only present on the ventricular-posterior side of the annulus: the ventricle wall intersection with the leaflets, their junction forming a valley or cavity onto which the catheter is guided and pushed to generate reaction forces permitting anchor insertions. This is reminiscent of suture-based annuloplasties, where only the posterior annulus is reshaped. Hence the same outcome can be expected. The proposed invention allows for sequentially installing interrelated anchors using a catheter system along the entire perimeter of the mitral valve annulus using atrial access. By doing so, it is expected that it will be possible to fully stop regurgitation with no redilation of the annulus, thus replicating the standard of care, ring annuloplasty.

Other objects, advantages and features of the present invention will become more apparent upon reading of the following non-restrictive description of preferred embodiments thereof, given by way of example only with reference to the accompanying drawings.

BRIEF DESCRIPTION FOR DRAWINGS

In the appended drawings:

FIG. 1, in a schematic view, illustrates an instrument in accordance with an embodiment of the present invention, the instrument being shown inserted in the body of a subject;

FIG. 2, in a perspective view, illustrates an instrument distal end section of the instrument shown in FIG. 1 in accordance with an embodiment of the present invention;

FIG. 3, in a side elevation view, illustrates an instrument distal end section of the instrument shown in FIG. 1 in accordance with another embodiment of the present invention;

FIGS. 4A to 4E, in bottom plan and transversal cross-sectional views, illustrate various movement sensor configurations and transversal cross-sectional configurations of the instrument distal end section shown in FIG. 3;

FIGS. 5A to 5D, in schematic views, illustrate successive steps in an example of use of the instrument distal end section shown in FIG. 2;

FIGS. 6A to 6E, in schematic views, illustrate successive steps in an example of use of the instrument distal end section shown in FIG. 3

Figure 7:
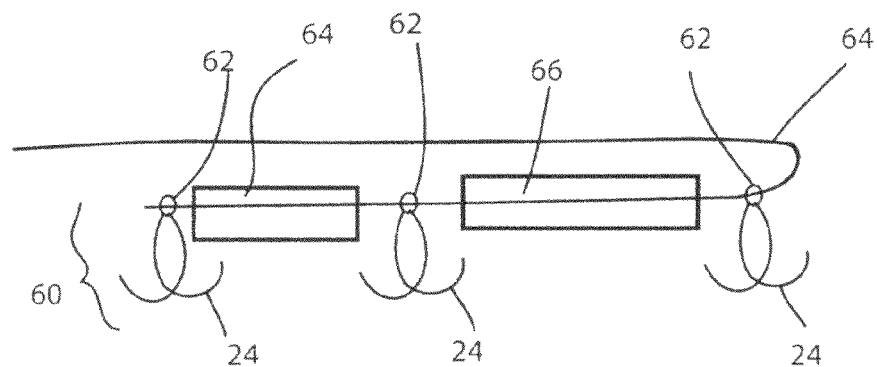
Figure 8:
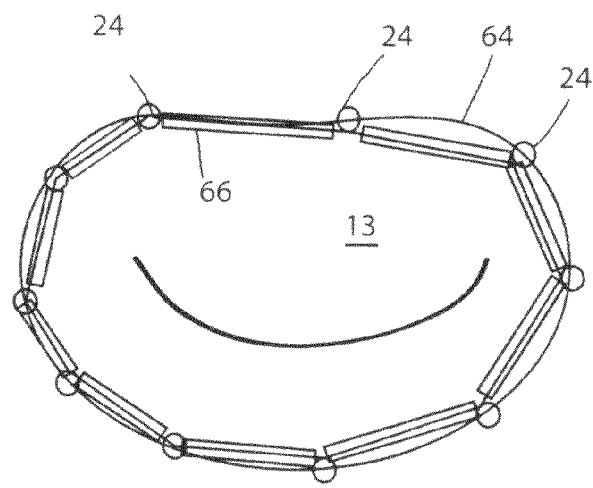
Figure 9:
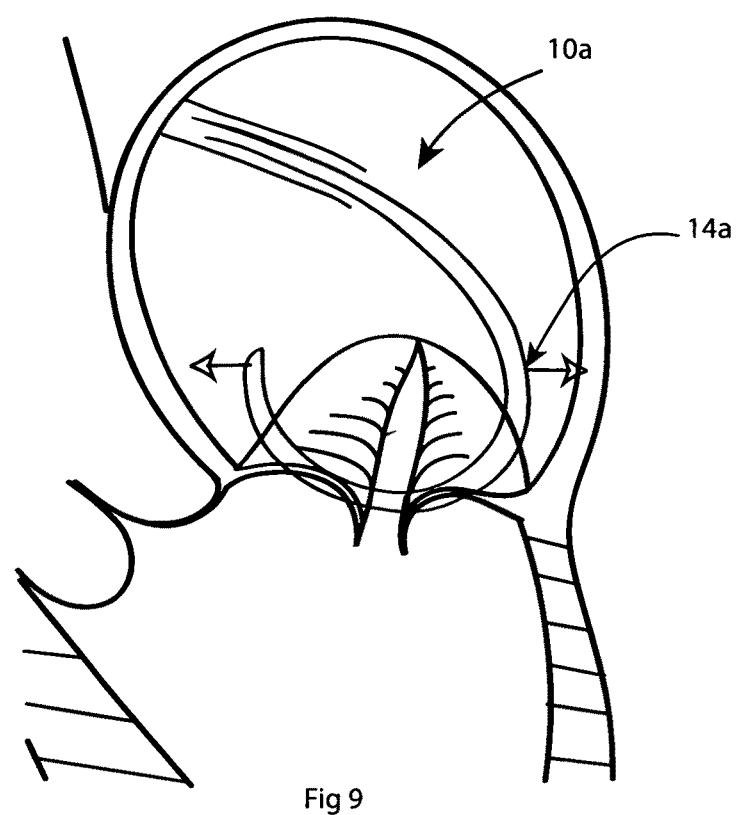
Figure 10:
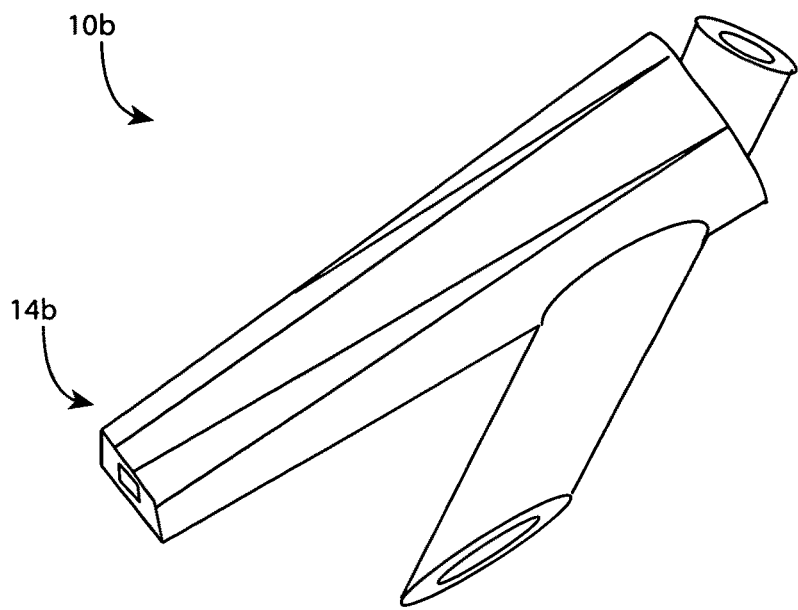
Figure 11:
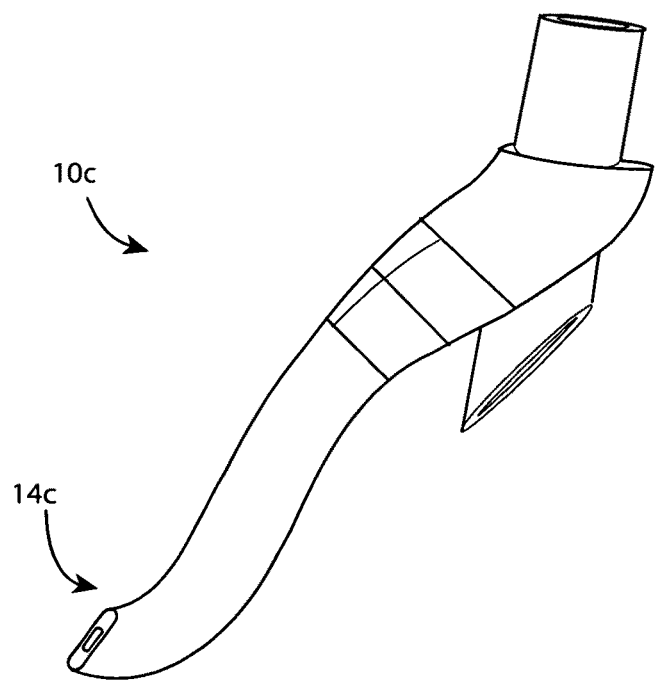

FIG. 7, in a schematic view, illustrates anchors and a wire usable to perform mitral valve annuloplasty using the instrument shown in FIG. 1;

FIG. 8, in an alternative schematic view, illustrates the anchors and the wire shown in FIG. 7;

FIG. 9, in a schematic view, illustrates an instrument distal end section of the instrument shown in FIG. 1 in accordance with another alternative embodiment of the present invention;

FIG. 10, in a schematic view, illustrates an instrument distal end section of the instrument shown in FIG. 1 in accordance with yet another alternative embodiment of the present invention; and FIG. 11, in a schematic view, illustrates an instrument distal end section of the instrument shown in FIG. 1 in accordance with yet another alternative embodiment of the present invention.

DETAILED DESCRIPTION

Referring to FIG. 1, there is shown an instrument 10 positionable with respect to a moving tissue, such as a body valve 13, in the body of a living subject 11 for performing a predetermined procedure on the living subject 11 at a predetermined location relative to the moving tissue. The instrument 10 is typically substantially elongated and defines an instrument proximal end section 12 and a substantially longitudinally opposed instrument distal end section 14. However, in alternative embodiments of the invention, elements of the instrument 10 described below are usable in differently shaped instruments.

As seen for example in FIG. 2, the instrument 10 includes a movement sensor 16 for sensing movements of the moving tissue. The instrument 10 also includes an effective portion 18 for performing the predetermined procedure when the effective portion 18 is at the predetermined location. An effective portion positioner 20, seen in FIG. 1, is provided for positioning the effective portion 18 in the living subject. The effective portion 18 is positionable using the effective portion positioner 20 in response to movement sensed by the movement sensor 16 for positioning the effective portion 18 at the predetermined location in order to perform the predetermined procedure. Typically, the effective portion 18 and the movement sensor 16 are provided substantially adjacent to the instrument distal end section 14 and the effective portion positioner 20 is provided, at least in part, substantially adjacent to the instrument proximal end section 12.

In some embodiments of the invention, the effective portion 18 includes an anchor implanting mechanism 22, shown for example in FIG. 2. The anchor implanting mechanism 22 is usable for implanting anchors 24 into living tissue. The anchor implanting mechanism 22 is described in further details hereinbelow. In alternative embodiments of the invention, the effective portion 18 is any other suitable effective portion 18, such as, for example, and energy delivery element for delivering electrical, ultrasound, or other energy at a predetermined location.

The instrument 10 is typically provided with a sheath 26 into which the remainder of the instrument 10 is slidable. In these embodiments, the instrument 10 is usable for performing percutaneous surgical procedures in a manner that is well known in the art. Typically, these procedures include guiding a guide wire through the blood vessels of a patient to a desired location. Afterwards, the sheath 26 can be slid over the guide wire up to the desired location. Finally, the guide wire is removed and the sheath 26 can be used for receiving any instrument that needs to be inserted up to a location adjacent to the predetermined location. In some embodiments of the invention, reaching the predetermined location includes piercing apertures into existing biological structures, such as the interatrial septum. Such procedures are well known in the art and will therefore not be described in further details.

In some embodiments of the invention, the instrument distal end section 14 is substantially J-shaped, as seen in FIG. 3. In these embodiments, it is possible to use pull wires 28 two change the orientation and shape of the instrument distal end section 14. In these embodiments, the instrument distal end section 14 is typically deformable between an operative configuration and a delivery configuration. In the operative configuration, shown in FIG. 3, the instrument distal end section 14 is usable for performing the predetermined procedure. In the delivery configuration, not shown in the drawings, the instrument distal end section 14 is substantially rectilinear and insertable into the sheath 26 so as to be movable there along.

The effective portion positioner 20 is the portion of the instrument 10 that allows for positioning of the effective portion 18 in the body of the subject. Such effective portion positioners 20 are well known in the art and include, depending on the exact embodiment of the invention, components that move the effective portion 18 inside the subject 11 and, in some embodiments of the invention, components that allow for orienting the effective portion 18 inside the subject 11. To that effect, in some embodiments of the invention, the effective portion positioner 20 deforms the instrument 10, for example substantially adjacent to or in the instrument distal end section 14. Such effective portion positioners 20 are well known in the art and would therefore not be described in further details.

FIG. 2 illustrates a movement sensor 16 in accordance with an embodiment of the present invention. The movement sensor 16 includes a deformable element 30 having a configuration, a rigidity, and dimensions such that the deformable element 30 is substantially freely deformable by the moving tissue when abutted against the moving tissue. A deformation sensor 32 is provided for sensing deformations of the deformable element 30. Therefore, when the movement sensors 16 is suitably located with respect to the moving tissue, the deformable element 30 will deform as the moving tissue moves, for example, when the moving tissue is a body valve, due to the passage of fluid and change of pressure through the body valve, and the deformation sensor 32 will sense such deformations and therefore indicate that the deformable element 30 is suitably located. However, if the deformable element 30 is not located at the right location, and does not contact the moving tissue, the deformable element 30 will not deform, or will deform in a manner different than it would if it were to contact to the moving tissue, and the deformation sensor 32 would therefore not sense deformations indicating that the deformable element 30 is suitably positioned. More details operation of this type of movement sensors 16 are provided hereinbelow.

Typically, the deformable element 30 is deformable in a predetermined plane. These embodiments facilitate interpretation of the movements sensed by the deformation sensor 32. However, in alternative embodiments of the invention, the deformable element 30 is deformable in at least two planes. In yet another embodiment, the deformable element 30 is freely-deformable to occupy a conical volume. Once it is deformed in one plane to a required degree, the effective portion is activated.

The deformable element 30 is typically substantially elongated and defines a deformable element proximal end 34 and a substantially opposed deformable element distant end 36. The deformable element proximal end 34 is fixed with respect to the effective portion 18 and, typically, located substantially adjacent to the effective portion 18 so as to facilitates interpretation of the data provided by the deformation sensor 32 to provide information indicative of the position of the effective portion 18. The deformable element distal end 36 is substantially freely movable relative to the effective portion 18. In alternative embodiments of the invention, the deformable element 30 takes any other suitable configuration and is secured to the remainder of the instrument 10 at any suitable location.

The deformable element 30 includes a series of deformable element segments 38 articulated to each other. In FIG. 2, four deformable element segments 38 are shown, but any other suitable number of deformable element segments 38 is within the scope of the present invention. The deformation sensor 32 includes segment movement sensors each provided for sensing movements of two adjacent deformable element segments 38 relatively to each other. For example, the deformable element segments 38 are substantially rigid and the segment movement sensors include angular position sensors indicative of an angle between two adjacent deformable element segments 38. Also, the proximal element segments 38 that it is proximalmost relatively to the effective portion 18 is hingedly attached to the remainder of the instrument 10.

In other embodiments of the invention, as shown in FIG. 3, the deformable element 30' is of a substantially continuous nature and does not include discrete segments articulated to each other. In these embodiments, the deformation sensor 32 includes for example a strain sensor provided for sensing in the deformable element 30. FIGS. 4A to 4E illustrate various example of transversal cross-sectional configurations of the deformable element 30' and corresponding strain sensor array configurations. The reader skilled in the art will readily appreciate that other combinations of strain sensor configurations and transversal cross-sectional configurations of the deformable element 30' are within the scope of the invention.

The deformable element can be constructed using the same manufacturing techniques used for catheter manufacturing. The material used covers a wide variety of polymers such as silicone, rubber latex and thermoplastic elastomers. By varying the thickness material composition and cross-section geometry, the element can be of different stiffness along its length. For example at the base it can be more rigid while at its tip it assumes greater flexibility in order to better mate with the moving tissue for example the valve leaflet.

In FIG. 4A, the deformable element 30' has a substantially semi-circular transversal cross-sectional configuration and includes substantially transversally oriented elongated strain sensors 40 that are substantially longitudinally spaced apart from each other along the deformable element 30'. In FIG. 4B, the deformable element 30' has a substantially oval transversal cross-sectional configuration and includes substantially chevron-shaped strain sensors 40 that are substantially longitudinally spaced apart from each other along the deformable element 30'. In FIG. 4C, the deformable element 30' has a substantially rectangular transversal cross-sectional configuration and includes substantially transversally oriented elongated strain sensors 40 that are substantially longitudinally spaced apart from each other along the deformable element 30'. In FIG. 4D, the deformable element 30' has a substantially hemi-circular transversal cross-sectional configuration with a V-shaped diameter and includes substantially chevron-shaped strain sensors 40 that are substantially longitudinally spaced apart from each other along the deformable element 30'. In FIG. 4E, the deformable element 30' has a substantially rounded square cross-sectional configuration and includes substantially square strain sensors 40 that are substantially uniformly distributed therealong.

In some embodiments of the invention, the strain sensors are replaced by an optical fiber extending along the deformable element 30'. Deformations of the optical fiber create changes in its optical properties that allow characterization of the shape of the deformable element 30'. An example of such optical fiber based deformation sensor is described at http://www.lunainnovations.com/technologies/shape-sensing.htm, the contents of which is hereby incorporated by reference in its entirety.

Figure 6A:
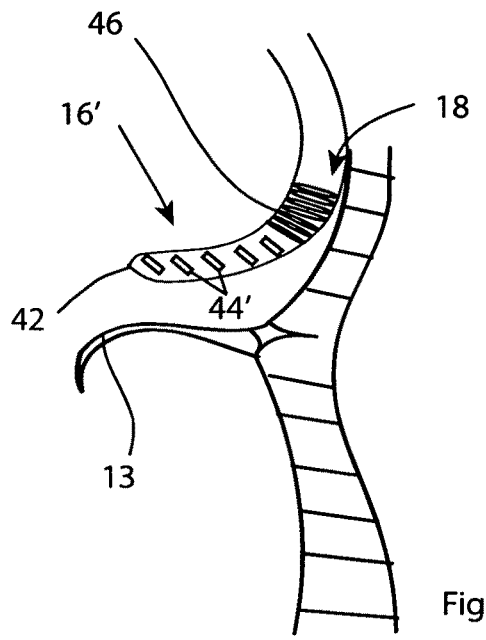

Referring for example to FIG. 6A, there is shown an alternative movement sensor 16' which includes a substantially rigid sensor support 42 and a movement sensing element 44 secured to the sensor support 42 for detecting movement substantially adjacent to the sensor support 42. The movement sensing element 44 includes one or more sensing elements selected from an electrical signal sensor, and ultrasound transducer, a softness sensor and a force sensor, among others. The movement sensing element 44 senses movements of biological structures adjacent to the sensor support 42, and can therefore provide information indicated of movement of moving tissue, such as valve leaflets, substantially adjacent to the sensor support 42. When the sensor support 42 is not suitably located, no such movements are registered by the sensing element 44. Typically, a substantially flexible section 46 having a rigidity substantially smaller than the rigidity of the sensor support 42 is provided between the sensor support 42 and the effective portion 18. In addition to facilitating positioning of the sensor support 42 relatively to adjacent tissue by deforming the flexible section 46, the flexible section 46 protects fragile biological structures by allowing the sensor support 42 to move when excessive force is exerted onto these structures.

Typically, the movement sensor 16' is substantially elongated and extends substantially outwardly from the remainder of the instrument 10. Substantially spaced apart movement sensing elements 44 are each secured to the sensor support 42 and are provided for detecting movement substantially adjacent to the sensor support 42. In embodiments wherein the sensor support 42 is substantially elongated, the movement sensing elements 44 are typically substantially longitudinally spaced apart from each other.

In yet other embodiments of the invention, positioning with respect to a moving valve is provided through thickness measurement in which a sensor measures the thickness of the underlying tissue. Since the valve is not of uniform thickness, position can be assessed by comparing thickness measurements at various locations along an instrument. For example, this is performed using laser-based sensing or sonar sensing, among other possibilities.

In some embodiments of the invention, as shown for example in FIG. 2, the effective portion 18 defines an effective portion distal tip 50 and an auxiliary position sensor 52 is operatively coupled to the effective portion 18 for providing position information indicative of a position of the effective portion 18. For example, the auxiliary position sensor 52 is provided substantially adjacent to the effective portion distal tip 50, but other locations are within the scope of the present invention. The auxiliary position sensor 52 increases accuracy in positioning of the effective portion 18. For example, the auxiliary position sensor 52 includes a force sensor or a softness sensor usable for discriminating different tissue types based respectively on their rigidity or softness Moreover in some embodiments, the deformable element 30 and the effective portion 18 are both effectively one element. For example the sensors are distributed along the deformable element and the anchors exit point is in the middle of that section.

FIGS. 5A to 5D illustrates successive steps in the use of the instrument 10 provided with the movement sensor 16 shown in FIG. 2. The method shown in FIGS. 5A to 5D is used for determining the position of the effective portion 18 of the instrument 10 relatively to a moving body valve 13 in living subjects using the movement sensor 16. In this example, the body valve 13 is the leaflet of the mitral valve. However, the present invention is usable for sensing the movements of any other suitable body parts, including any other body valve or any other cardiac valve.

Figure 5A:
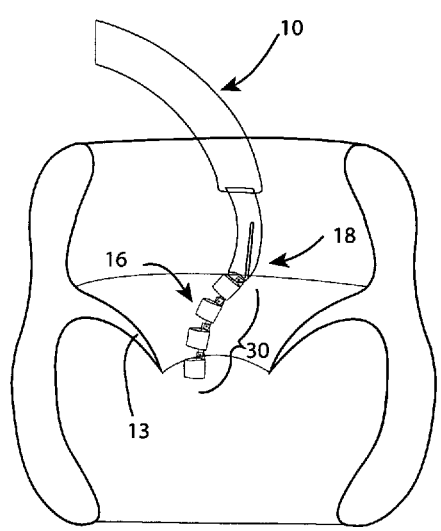

First, as shown in FIG. 5A, the movement sensor 16 is inserted into the living subject up to a location adjacent to the body valve 13. In FIG. 5A, the movement sensors 16 has been inserted in the left atrium of the heart of the subject 11. Since the relative position of the movement sensors 16 and the effective portion 18 is fixed, positioning the effective portion 18 and orienting properly the instrument 10 then automatically positions the movement sensor 16 so that the movement sensor 16 and the effective portion 18 are in a predetermined positional relationship relative to each other. In FIG. 5A, the movement sensor 16 is shown with the effective portion 18 provided in a substantially spaced apart relationship relatively to the body valve 13.

Figure 5B:
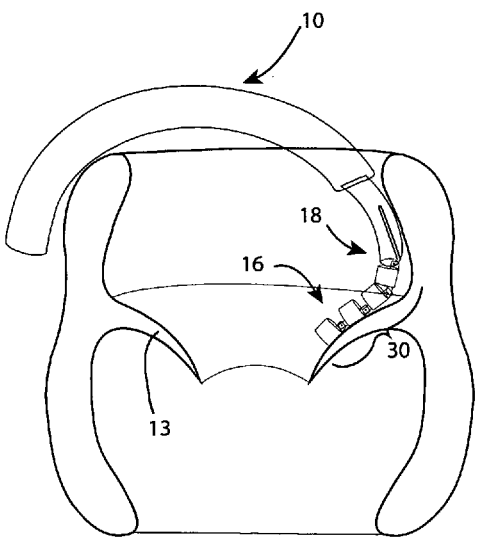

Once the movement sensor 16 has been positioned, movement sensor movement information indicative of movement of living tissue substantially adjacent to the movement sensor 16 is generated and information is sent for reception outside of the subject 11, were the position of the effective portion 18 relatively to the moving body valve 13 is assessed on the basis of the movement information. In FIG. 5B, the movement sensor 16 is shown with only a portion of the movement sensor 16 abutting against the body valve 13. Sensing deformation of the movement sensor 16 then result in information indicating that this movement sensor 16 is not entirely positioned onto the body valve 13, which therefore requires that the effective portion 18 be moved inside the subject 11.

Figure 5C:
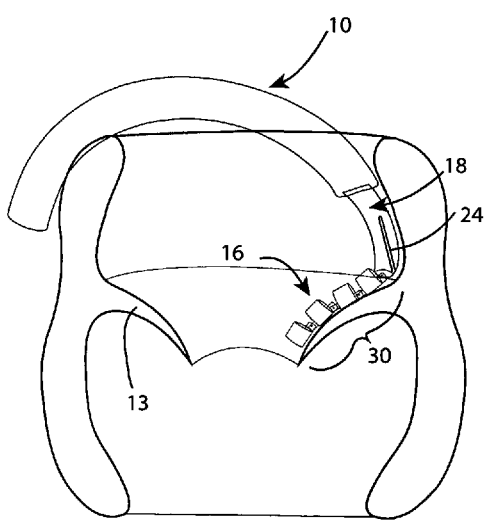
Figure 5D:
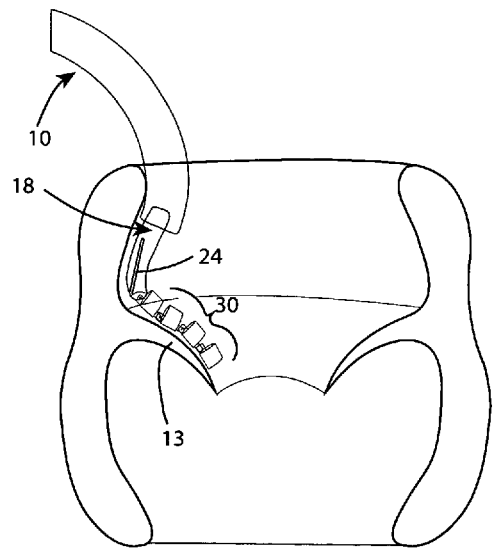

In FIG. 5C the, the movement sensor 16 is entirely contacting the body valve 13 and therefore deforms along with the body valve 13, for example as the heart of the subject 11 beats. This deformation generates the movement information indicative of a proper positioning of the movement sensor 16 and the effective portion 18. More specifically, relatively large amplitude movements having a periodic variation in time similar to the period of movement of the body valve 13 are sensed by the movement sensor 16. In consequence, the hinge point representing the mitral annulus is identified. The effective portion 18 is then usable for implanting an anchor 24 into the heart of the subject 11. Use of this anchor 24 is described in further details hereinbelow. In FIG. 5D, the movement sensor 16 and the effective portion 18 have been moved to another location to implant another anchor 24 at this other location.

In another embodiment, the deformable element 30 is covered by an array of electrical signal sensors such as electrode which helps mapping the electrical characteristics of the underlining tissue, such as resistance, capacitance, or voltage and current potentials. Since the deformable section 30 is always in contact with the tissue the reading should identify any change in underlying tissue electrical properties. For example, in the case of the mitral valve, the sensor would pick up electrical potential from the atrium those of which will start to attenuate at the annulus and disappear on the leaflet. When the sensors picks up this electrical transition, the annulus is identified and the effective portion is positioned on the annulus and activated.

Figure 6B:
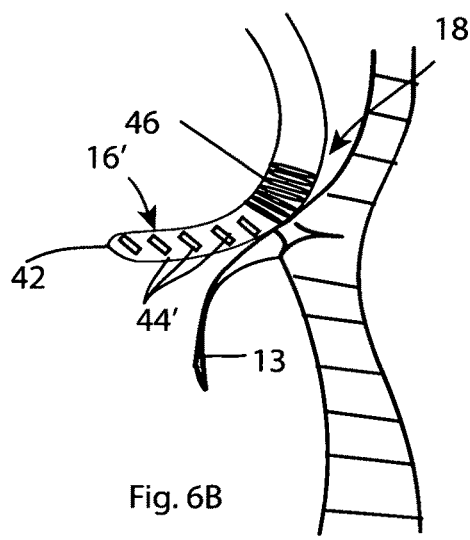
Figure 6C:
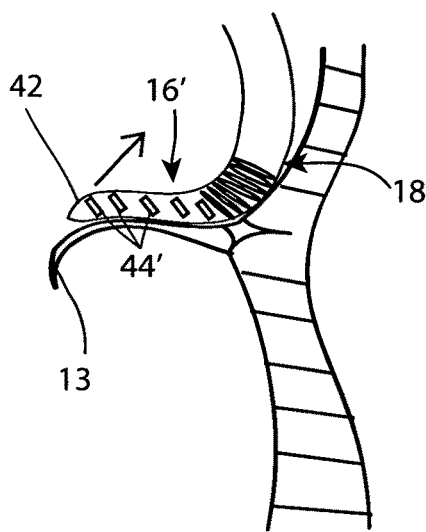
Figure 6D:
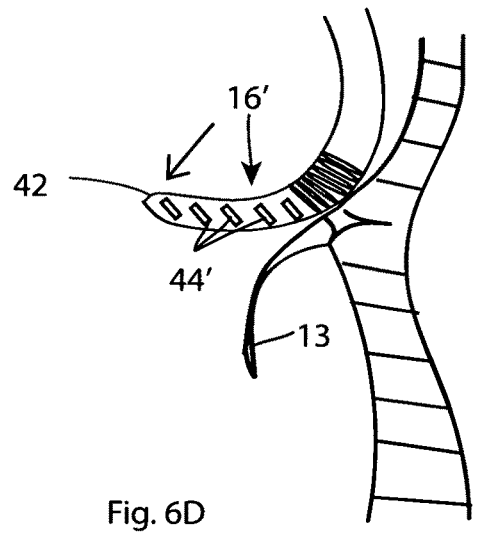
Figure 6E:
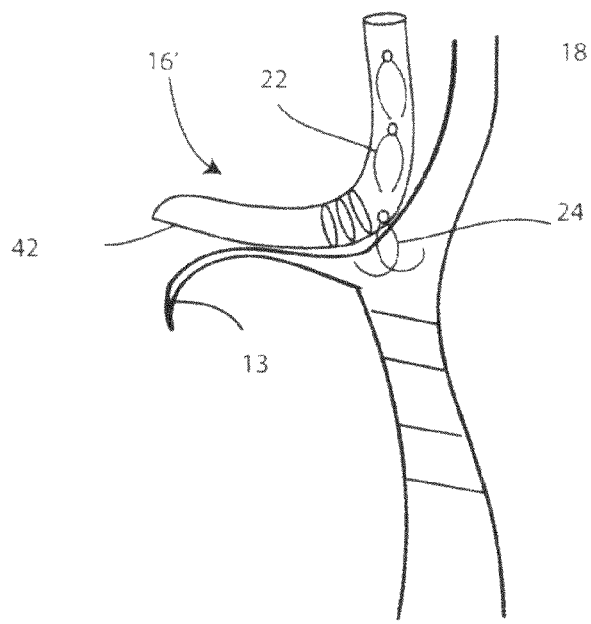

FIGS. 6A to 6E illustrate movement detection using the alternative movement sensor 16'. In these embodiments, the body valve 13 moves independently of the movement sensor 16' and these movements are detected by the movements detectors 44. In FIG. 6A, the sensor support 42 is spaced apart from the body valve 13 at all times during its movement cycle and the movement sensing elements 44 detect that the body valve 13 never contacts the sensor support 42. In FIG. 6B, the sensor support 42 has been moved to be adjacent to the body valve 13, but is oriented such that movements of the body valve 13 are restricted. In this position, only some of the movement sensing elements 44 detect a cycle of movement of the body valve 13 and the other movement sensing elements 44 detect no such movements. In FIGS. 6C and 6D, after having been moved to another location, the sensor support 42 is correctly positioned such that the body valve 13 moves substantially freely and all movement sensing elements 44 register a periodic movement of the body valve 13 between full contact therewith and a spaced apart relationship relatively thereto. As seen in FIG. 6E, in this position, the anchors 24 can be inserted in the tissue adjacent the body valve 13.

FIG. 7 illustrates a series of anchors 24 each including an anchor body 60 insertable in biological tissue and a ring 62 extending therefrom. A wire 64 is inserted through the rings 62 of a plurality of anchors 24. In some embodiments of the invention, relatively soft padding material 66, such as a foam, is provided on the wire 64 between the rings 62. Typically, this structure is pre-assembled and inserted in the effective portion 18 for successively implanting the interlinked anchors 24. As seen in FIG. 8, these anchors can be implanted around a body valve 13 so that, by pulling on the wire 64, the diameter of the body valve 13 can be reduced. The padding material 66 prevents, or reduces, body fluid flow between the wire 64 and adjacent biological structures, which can help in patient recovery by facilitating embedding of the wire 64 in the biological structures of the subject 11.

As seen respectively in FIGS. 9, 10 and 11, instruments 10a, 10b and 10c having differently shaped instrument distal end sections 14a, 14b and 14c in a deployed configuration are within the scope of the invention. The instrument distal end sections 14a, 14b and 14c are respectively substantially U-shaped, substantially rectilinear and substantially flattened-Z shaped. The instrument distal end section 14a is advantageous to further stabilize the instrument 10 in the atrium by abutting against two opposed portions of the atrium. Instrument distal end sections 14b and 14c are advantageous to increase the contact surface area between the instrument distal end sections 14b and 14c and the mitral valve.

Although the present invention has been described hereinabove by way of preferred embodiments thereof, it can be modified, without departing from the spirit and nature of the subject invention as defined in the appended claims.

What is claimed is:

1. An instrument positionable with respect to a body valve in the body of a living subject for implanting anchors into living tissue at a predetermined location relative to said body valve, said instrument comprising:
    a movement sensor for sensing movements of said body valve;
    an effective portion for implanting anchors when said effective portion is at said predetermined location, said effective portion including an anchor implanting mechanism for implanting said anchors at said predetermined location; and
    an effective portion positioner for positioning said effective portion in said living subject;
    whereby said effective portion is positionable using said effective portion positioner in response to said movements sensed by said movement sensor for positioning said effective portion at said predetermined location in order to use said anchor implanting mechanism for implanting said anchors at said predetermined location;
    wherein said movement sensor includes
        a deformable element having a configuration, a rigidity and dimensions such that said deformable element is substantially freely deformable by said valve when abutting against said valve; and
        a deformation sensor for sensing deformations of said deformable element.

2. An instrument as defined in claim 1, wherein said deformable element is deformable in a predetermined plane.

3. An instrument as defined in claim 1, wherein said deformable element is substantially elongated, said deformable element defining a deformable element proximal end and a substantially opposed deformable element distal end, said deformable element proximal end being fixed with respect to said effective portion and located substantially adjacent to said effective portion and said deformable element distal end being substantially freely movable relative to said effective portion.

4. An instrument as defined in claim 3, wherein said deformable element includes a series of deformable element segments articulated to each other and said deformation sensor includes segments movement sensors for sensing movements of said deformable element segments relative to each other.

5. An instrument as defined in claim 1, wherein said deformation sensor includes a strain sensor for sensing strain in said deformable element.

6. An instrument as defined in claim 1, wherein said deformation sensor includes an electrical sensor for sensing electric activity in adjacent tissue.

7. An instrument as defined in claim 1, wherein said deformable element is hingedly attached to the remainder of said instrument.

8. An instrument as defined in claim 1, wherein said instrument is substantially elongated and defines an instrument proximal end section and a substantially longitudinally opposed instrument distal end section, said effective portion and said movement sensor being provided substantially adjacent to said instrument distal end section, and said effective portion positioner being provided, at least in part, substantially adjacent to said instrument proximal end section.

9. An instrument as defined in claim 8, wherein said instrument distal end section is substantially J-shaped.

10. An instrument as defined in claim 8, wherein said distal end section is deformable between an operative configuration and a delivery configuration, wherein, in said operative configuration, said distal end section is usable for performing said predetermined procedure, and, in said delivery configuration, said distal end section is insertable through a substantially elongated sheath so as to be movable therealong.

11. An instrument as defined in claim 1, wherein said instrument includes an auxiliary position sensor operatively coupled to said effective portion for providing position information indicative of a position of said effective portion.

12. An instrument as defined in claim 11, wherein said effective portion defines an effective portion distal tip, said auxiliary position sensor being provided substantially adjacent to said effective portion distal tip.

13. An instrument as defined in claim 11, wherein said auxiliary position sensor includes at least one of a softness sensor, a force sensor and an electrical sensor.

14. An instrument positionable with respect to a body valve in the body of a living subject for performing a predetermined procedure on said living subject at a predetermined location relative to said body valve, said instrument comprising:
    a movement sensor for sensing movements of said body valve, said movement sensor including a deformable element having a configuration, a rigidity and dimensions such that said deformable element is substantially freely deformable by said valve when abutting against said valve, and a deformation sensor for sensing deformations of said deformable element;
    an effective portion for performing said predetermined procedure when said effective portion is at said predetermined location; and
    an effective portion positioner for positioning said effective portion in said living subject;
    wherein said deformable element is substantially elongated, said deformable element defining a deformable element proximal end and a substantially opposed deformable element distal end, said deformable element proximal end being fixed with respect to said effective portion and located substantially adjacent to said effective portion and said deformable element distal end being substantially freely movable relative to said effective portion;
    whereby said effective portion is positionable using said effective portion positioner in response to said movements sensed by said movement sensor for positioning said effective portion at said predetermined location in order to perform said predetermined procedure.

15. An instrument as defined in claim 14, wherein said deformable element includes a series of deformable element segments articulated to each other and said deformation sensor includes segments movement sensors for sensing movements of said deformable element segments relative to each other.

* * * * *